(12) United States Patent
Tanaka et al.

(10) Patent No.: US 7,083,687 B2
(45) Date of Patent: Aug. 1, 2006

(54) SUPER-ELASTIC TITANIUM ALLOY FOR MEDICAL USES

(75) Inventors: Toyonobu Tanaka, Kanagawa (JP); Hiroshi Horikawa, Kanagawa (JP); Shuichi Miyazaki, Ibaraki (JP); Hideki Hosoda, Kanagawa (JP)

(73) Assignee: Furukawa Techno Material Co., Ltd., Hiratsuka (JP)

( * ) Notice: Subject to any disclaimer, the term of this patent is extended or adjusted under 35 U.S.C. 154(b) by 0 days.

(21) Appl. No.: 11/085,336

(22) Filed: Mar. 21, 2005

(65) Prior Publication Data

US 2005/0161130 A1 Jul. 28, 2005

Related U.S. Application Data

(62) Division of application No. 10/396,917, filed on Mar. 25, 2003, now Pat. No. 6,921,441.

(30) Foreign Application Priority Data

Apr. 4, 2002 (JP) .............................. 2002-102531

(51) Int. Cl.
*C22F 1/18* (2006.01)
*C22F 1/02* (2006.01)
(52) U.S. Cl. ...................................... 148/563; 148/671
(58) Field of Classification Search ................ 148/563, 148/671, 669, 670
See application file for complete search history.

(56) References Cited

U.S. PATENT DOCUMENTS

| | | | | |
|---|---|---|---|---|
| 4,737,341 A | * | 4/1988 | Barber | ........................ 420/419 |
| 5,904,480 A | | 5/1999 | Farzin-Nia et al. | |
| 5,954,724 A | | 9/1999 | Davidson | |
| 6,053,993 A | * | 4/2000 | Reichman et al. | ........... 148/421 |
| 6,258,182 B1 | * | 7/2001 | Schetky et al. | ............... 148/402 |

FOREIGN PATENT DOCUMENTS

JP 05 295498 11/1993
WO 99/45161 9/1999

OTHER PUBLICATIONS

"Metals Handbook: Desk Edition", ASM International, 1998, p. 578-581.*

* cited by examiner

*Primary Examiner*—George Wyzsomierski
*Assistant Examiner*—Janelle Morillo
(74) *Attorney, Agent, or Firm*—Frederick L. Tolhurst, Esq.; Cohen & Grigsby, P.C.

(57) ABSTRACT

A super-elastic titanium alloy for medical use consisting essentially of:
molybdenum (Mo) as a β stabilizer element of titanium (Ti): from 2 to 12 at %; an α stabilizer element of the titanium (Ti): from 0.1 to 14 at %; and the balance being titanium (Ti) and inevitable impurities. The α stabilizer element is at least one element selected from the group consisting of aluminum (Al), gallium (Ga) and germanium (Ge).

8 Claims, 3 Drawing Sheets

<TABLE 1>

| No. | Composition (at%) | | | Shape Memory Effects | Remarks |
|---|---|---|---|---|---|
| | Ti | Mo | Ga | | |
| a-1 | balance | 5 | 2 | O | Examples of Present Invention |
| a-2 | balance | 5 | 8 | O | |
| a-3 | balance | 5 | 12 | O | |
| a-4 | balance | 10 | 2 | O | |
| a-5 | balance | 10 | 8 | O | |
| a-6 | balance | 10 | 12 | O | |
| a-7 | balance | 0 | 4 | × | Comparative Examples |
| a-8 | balance | 0 | 12 | × | |
| a-9 | balance | 5 | 16 | × | |
| a-10 | balance | 10 | 16 | × | |
| a-11 | balance | 15 | 4 | × | |
| a-12 | balance | 15 | 12 | × | |

FIG. 2  <TABLE 1>

| No. | Composition (at%) | | | Shape Memory Effects | Remarks |
|---|---|---|---|---|---|
| | Ti | Mo | Ga | | |
| a-1 | balance | 5 | 2 | O | Examples of Present Invention |
| a-2 | balance | 5 | 8 | O | |
| a-3 | balance | 5 | 12 | O | |
| a-4 | balance | 10 | 2 | O | |
| a-5 | balance | 10 | 8 | O | |
| a-6 | balance | 10 | 12 | O | |
| a-7 | balance | 0 | 4 | × | Comparative Examples |
| a-8 | balance | 0 | 12 | × | |
| a-9 | balance | 5 | 16 | × | |
| a-10 | balance | 10 | 16 | × | |
| a-11 | balance | 15 | 4 | × | |
| a-12 | balance | 15 | 12 | × | |

FIG. 3  <TABLE 2>

| No. | Composition (at%) | | | Shape Memory Effects | Remarks |
|---|---|---|---|---|---|
| | Ti | Mo | Al | | |
| b-1 | balance | 5 | 4 | O | Examples of Present Invention |
| b-2 | balance | 5 | 8 | O | |
| b-3 | balance | 5 | 12 | O | |
| b-4 | balance | 10 | 4 | O | |
| b-5 | balance | 10 | 8 | O | |
| b-6 | balance | 10 | 12 | O | |
| b-7 | balance | 0 | 4 | × | Comparative Examples |
| b-8 | balance | 0 | 12 | × | |
| b-9 | balance | 5 | 2 | × | |
| b-10 | balance | 5 | 16 | × | |
| b-11 | balance | 10 | 2 | × | |
| b-12 | balance | 10 | 16 | × | |
| b-13 | balance | 15 | 4 | × | |
| b-14 | balance | 15 | 12 | × | |

FIG. 4

<TABLE 3>

| No. | Composition (at%) | | | Shape Memory Effects | Remarks |
|---|---|---|---|---|---|
| | Ti | Mo | Ge | | |
| c-1 | balance | 5 | 2 | ○ | Examples of Present Invention |
| c-2 | balance | 5 | 6 | ○ | |
| c-3 | balance | 10 | 2 | ○ | |
| c-4 | balance | 10 | 6 | ○ | |
| c-5 | balance | 0 | 2 | × | Comparative Examples |
| c-6 | balance | 0 | 6 | × | |
| c-7 | balance | 5 | 10 | × | |
| c-8 | balance | 10 | 10 | × | |
| c-9 | balance | 15 | 2 | × | |
| c-10 | balance | 15 | 6 | × | |

SUPER-ELASTIC TITANIUM ALLOY FOR MEDICAL USES

CROSS REFERENCE

This application is a divisional of U.S. patent application Ser. No. 10/396,917 filed on Mar. 25, 2003 now U.S. Pat. No. 6,921,441.

BACKGROUND OF THE INVENTION

1. Field of the Invention

The present invention relates to a super-elastic Ti alloy for medical uses. Particularly, the present invention relates to a Ti—Mo—Ga alloy, a Ti—Mo—Al alloy and a Ti—Mo—Ge alloy which exhibit super elastic properties and which are useful for medical applications.

2. Related Art

Recently, many attempts have been made to find medical applications of an alloy with a super elastic property. For example, a Ti—Ni alloy has properties of high strength, excellent abrasion resistance, good corrosion resistance, good biocompatibility and the like, and is used in a variety of fields as an alloy for medical uses.

As an example, a Ti—Ni alloy wire used in an orthodontic appliance has a super-elastic region where constant loading is maintained irrespective of changes in deformation of the wire. Since this wire can impart necessary forces constantly even after teeth are moved by teeth-straightening, it is usable as an orthodontic wire. In addition, such a alloy is also usable in implants for plastic surgery with the full use of its excellent recoverability, and usable for medical catheters, guide wires or the like with the full use of its reasonable formability and stiffness.

Such a Ni—Ti alloy is described in the Japanese Provisional Patent Publication No. 5-295498, which consists of from 49.5 to 51.5% Ni, 1.8% or less Cr and the balance Ti. This alloy is made by casting, hot working and then, repeating annealing and cold working.

In these days, concerns are rising over biomedical materials having a Ni metal which, suspected of causing allergic symptom, may be leached out within the living body. Since a Ni—Ti alloy contains Ni as a principal element, the Ni—Ti alloy may cause anxiety about allergy, and therefore, demands for safer alloys usable in medical applications are growing.

In other words, demands are growing for alloys which contain no element such as Ni that may cause an allergic problem to the living body but have good biocompatibility.

SUMMARY OF THE INVENTION

It is an object of the present invention to provide a Ni-free alloy which is useful for medical applications, or a titanium alloy which has improved biocompatibility as well as super-elastic properties.

A first embodiment of the super-elastic titanium alloy for medical uses of the present invention is a super-elastic titanium alloy for medical use consisting essentially of:
  molybdenum (Mo) as a β stabilizer element of titanium (Ti)
    :from 2 to 12 at %;
  an α stabilizer element of the titanium (Ti)
    : from 0.1 to 14 at %; and
  the balance being titanium (Ti) and inevitable impurities.

A second embodiment of the super-elastic titanium alloy for medical uses of the present invention is a super-elastic titanium alloy in which said α stabilizer element is at least one element selected from the group consisting of aluminum (Al), gallium (Ga) and germanium (Ge).

A third embodiment of the super-elastic titanium alloy for medical uses of the present invention is a super-elastic titanium alloy in which said α stabilizer element is from 0.1 to 14 at % gallium (Ga).

A fourth embodiment of the super-elastic titanium alloy for medical uses of the present invention is a super-elastic titanium alloy in which said α stabilizer element is from 3 to 14 at % aluminum (Al).

A fifth embodiment of the super-elastic titanium alloy for medical uses of the present invention is a super-elastic titanium alloy in which said α stabilizer element is from 0.1 to 8 at % germanium (Ge).

A sixth embodiment of the super-elastic titanium alloy for medical uses of the present invention is a super-elastic titanium alloy in which said α stabilizer element is from 3 to 9 at % aluminum (Al) and a content of said molybdenum (Mo) is from 4 to 7 at %.

A seventh embodiment of the super-elastic titanium alloy for medical uses of the present invention is a super-elastic titanium alloy as claimed in claim 2, wherein said α stabilizer element is from 1 to 4 at % gallium (Ga) and a content of said molybdenum (Mo) is from 4 to 7 at %.

An eighth embodiment of the super-elastic titanium alloy for medical uses of the present invention is a super-elastic titanium alloy in which said α stabilizer element is from 1 to 4 at % germanium (Ge) and a content of said molybdenum (Mo) is from 4 to 7 at %.

A ninth embodiment of the super-elastic titanium alloy for medical uses of the present invention is a super-elastic titanium alloy in which said super-elastic titanium alloy is a β solid solution titanium alloy having an orthorhombic crystalline structure.

A first embodiment of a method for making a super-elastic titanium alloy for medical use of the present invention is a method for making a super-elastic titanium alloy for medical use comprising the steps of:
  preparing a titanium alloy ingot which consists essentially of:
    molybdenum (Mo) as a β stabilizer element of titanium (Ti)
      :from 2 to 12 at %;
    as an α stabilizer element of the titanium (Ti), at least one element selected from the group consisting of aluminum (Al), gallium (Ga) and germanium (Ge)
      :from 0.1 to 14 at %; and
    the balance being titanium (Ti) and inevitable impurities,
  subjecting the ingot to a homogenized heat treatment in a vacuum environment or an inert gas environment at a temperature ranging from 1,000 degree to 1,200 degree, and cooling the ingot quickly to a room temperature;
  after cooling the ingot to the room temperature, cold working the ingot to prepare a sheet; and
  subjecting the sheet to a solution heat treatment in the vacuum environment or the inert gas environment at a temperature ranging from 600 degree to 1,100 degree.

A second embodiment of the method for making a super-elastic titanium alloy for medical use of the present invention is a method in which the α stabilizer element of the titanium alloy ingot is from 0.1 to 14 at % gallium (Ga).

A third embodiment of the method for making a super-elastic titanium alloy for medical use of the present invention is a method in which the α stabilizer element of the titanium alloy ingot is from 3 to 14 at % aluminum (Al).

A fourth embodiment of the method for making a super-elastic titanium alloy for medical use of the present invention is a method in which the α stabilizer element of the titanium alloy ingot is from 0.1 to 8 at % germanium (Ge).

A fifth embodiment of the method for making a super-elastic titanium alloy for medical use of the present invention is a method in which a content of the molybdenum (Mo) is from 4 to 7 at % and the α stabilizer element of the titanium alloy ingot is from 3 to 9 at % aluminum (Al).

A sixth embodiment of the method for making a super-elastic titanium alloy for medical use of the present invention is a method in which a content of the molybdenum (Mo) is from 4 to 7 at % and the α stabilizer element of the titanium alloy ingot is from 1 to 4 at % gallium (Ga).

A seventh embodiment of the method for making a super-elastic titanium alloy for medical use of the present invention is a method in which a content of the molybdenum (Mo) is from 4 to 7 at % and the α stabilizer element of the titanium alloy ingot is from 1 to 4 at % germanium (Ge).

An eighth embodiment of the method for making a super-elastic titanium alloy for medical use of the present invention is a method in which a time of the homogenized heat treatment ranges from 10 to 48 hours.

A ninth embodiment of the method for making a super-elastic titanium alloy for medical use of the present invention is a method in which a time of the solution heat treatment ranges from 1 minute to 10 hours.

BRIEF DESCRIPTION OF THE DRAWINGS

FIG. 2 is a table which provides a listing of compositions of a Ti—Mo—Ga alloy and their evaluations;

FIG. 3 is a table which provides a listing of compositions of a Ti—Mo—Al alloy and their evaluations; and FIG. 4 is a table which provides a listing of compositions of a Ti—Mo—Ge alloy and their evaluations.

DETAILED DESCRIPTION OF THE INVENTION

Figure 1:
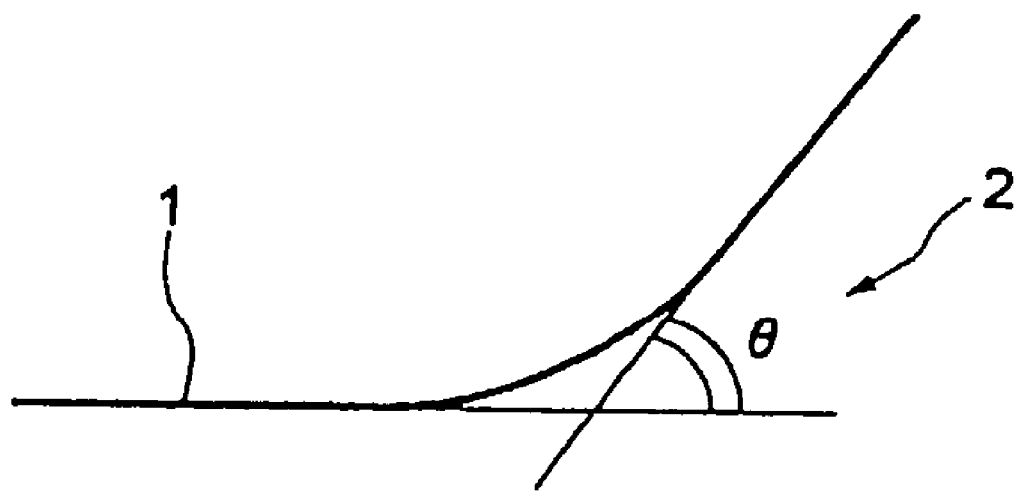
FIG. 1 is a view for explaining how to measure a bend angle.

Embodiments of the present invention will be described in detail below. An alloy of the present invention is a titanium alloy which, in order to realize thermo-elastic martensite transformation, contains alloying elements of: molybdenum (Mo) which is a β stabilizer element for lowering a martensite transformation temperature; and at least one selected from the group consisting of gallium (Ga), aluminum (Al) and germanium (Ge) which are α stabilizer elements, or more specifically, a super-elastic titanium alloy for medical uses to be substituted for a Ti—Ni alloy.

Here, a β stabilizer element of the present invention is not limited to Mo, but may be any β stabilizer element that can lower a martensite transformation temperature. For example, elements such as niobium (Nb), Fe and the like can be replaced for Mo to obtain a super-elastic titanium alloy. Besides, an α stabilizer element is not limited to Ga, Al or Ge but may be tin (Sn), oxygen (O) or the like to obtain a super-elastic titanium alloy.

Conventional Ni—Ti alloys are shape memory alloys having "shape memory effects" such that when an alloy having a certain shape is transformed to a different shape from the original shape at a lower temperature, and then heated above a temperature for stabilizing a high temperature phase (parent phase, here), the reverse transformation (phase transformation associated with heating and unloading) occurs and thereby, the alloy recovers the original shape.

All alloys that undergo martensite transformation do not exhibit shape memory effects. Alloys that undergo thermo-elastic martensite transformation (i.e., Ni—Ti alloys are included) recover their original shapes upon heating as far as the deformation appears within certain limits. Alloys according to the present invention are titanium alloys having such a property, or more specifically, titanium alloys to which Mo is added, and Ga, Al or Ge is further added thereto.

As one embodiment of the present invention a Ti—Mo—Ga alloy is now described. When Mo as an β stabilizer element is added to Ti, a temperature of α phase/β phase transformation is shifted toward a lower temperature side, which allows to obtain an alloy with a stable β phase structure even at room temperature. This is because rapid cooling from a β phase temperature causes the β phase to be remained, and for the case of a homogeneous solid-solution type binary Mo—Ti alloy, Mo content is said to be about 20 at % at the minimum. For the case of an alloy with Mo content about 20 at % or less, there occurs martensite transformation even if the alloy is rapidly cooled, thus it cannot be said that the β phase is completely remained.

Such a martensite has two types of α phase, that is, α' phase and α" phase, of which crystalline structures are hexagonal and orthorhombic, respectively. In order for an alloy to exhibit super-elastic effects, the martensite transformation has to be thermo-elastic martensite transformation. Between these two martensitic α phases, the α" phase is known as one capable of being thermo-elastic martensite transformation.

When Ga is added to Ti, it is said that Ga functions as an α stabilizer element, extending α phase region so as to improve the strength at room temperature. Then, development work has been advanced on super-elastic β phase type solid solution titanium alloys having the composition of Ti to which Mo as a β stabilizer element for lowering martensite transformation temperature and Ga as a α stabilizer element are added, which undergoes thermo-elastic martensite transformation upon rapid cooling. As a result, the super-elastic β phase type solid solution titanium alloys with the composition mentioned below has been developed.

In the present invention, Mo content is limited within the range of from 2 to 12 at %. This is because the super elastic performance is deteriorated when Mo content is below 2 at % or over 12 at %. In other words, there occurs plastic deformation within a deformed alloy, which makes it difficult for the alloy to recover its original shape. Preferable Mo content is within the range of from 4 to 7 at %. More preferably, Mo content is within the range of from 5 to 6 at %.

Ga content as an α stabilizer element is limited within the range of from 0.1 to 14 at %. This is because super elastic performance is deteriorated when Ga content is below 0.1 at % or over 14 at %. In other words, there occurs plastic deformation within a deformed alloy, which makes it difficult for the alloy to recover its original shape. Preferable Ga content is within the range of from 1 to 4 at %. More preferably, Ga content is within the range of from 3 to 4 at %.

Accordingly, a Ti alloy containing Mo from 2 to 12 at % and Ga from 1 to 14 at % becomes a super-elastic β phase type solid solution titanium alloy. Therefore, a crystalline structure of the rapidly cooled titanium alloy becomes orthorhombic with excellent transformation behavior, which facilitates hot working and cold working, thereby reducing working cost as compared with Ni—Ti alloys. A method for manufacturing a Ti—Mo—Ga alloy is described below as one example, however, this is not for limiting the scope of the present invention.

First, metals as given alloying components are melted in a consumable electrode arc melting furnace and cast into required shapes to prepare ingots. Then, in order to remove segregation, thus prepared ingots are subjected to homogenized heat treatment under the following conditions. Heat treatment environments are preferably vacuum or inert gas environments. Heat treatment temperatures preferably ranges from 1,000 degree to 1,200 degree. Regarding heat treatment time, retention time is set within the range of from 10 to 48 hours. After being homogenized heat treated, the ingots were rapidly cooled down to a room temperature with the use of oil or water.

The above-mentioned conditions for homogenized heat treatment are selected for the following reasons. The vacuum and inert gas environments are selected for preventing Ti from reacting to oxygen so as to avoid embrittlement of Ti. In addition, homogenized heat treatment performed below 1,000 degree may cause insufficient homogenization, while homogenized heat treatment performed over 1,200 degree may cause partial melting due to the too high temperature, reducing economic efficiency. When the retention time of less than 10 hours may cause insufficient homogenization while the retention time of more than 48 hours may reduce economic efficiency.

Then, the heat treated and rapidly cooled ingots are cold worked to prepare thin sheets. For the purpose of solid solution heat treatment of alloying elements, the thin sheets are subjected to solution heat treatment under the following conditions. Heat treatment environments are preferably vacuum or inert gas environments. Heat treatment temperatures preferably ranges from 600 degree to 1,200 degree. Regarding heat treatment time, retention time is set within the range of from 1 minute to 10 hours.

The above-mentioned conditions for solution heat treatment are selected for the following reasons. The vacuum and inert gas environments are selected for preventing Ti from reacting to oxygen so as to avoid embrittlement of Ti. In addition, heat treatment temperatures performed below 600 degree may cause insufficient heat treatment while temperatures over 1200 degree may reduce economic efficiency. When the retention time of less than 1 minute may cause insufficient heat treatment while the retention time of more than 10 hours may reduce economic efficiency. Then, appropriate working or heat treatment are performed to obtain super-elastic titanium alloy with α phase finely precipitated.

As another embodiment of the present invention a Ti—Mo—Al alloy is now described. Effects of Mo added to Ti are the same as described in the above embodiment.

When Al is added to Ti, Al functions as an α stabilizer element, extending α phase region so as to improve the strength at room temperature. Then, development work has been advanced on super-elastic β solid solution titanium alloys having the composition of Ti to which Mo as a β stabilizer element for lowering martensite transformation temperature and Al as a α stabilizer element are added, which undergoes thermo-elastic martensite transformation upon rapid cooling. As a result, the super-elastic β solid solution titanium alloys with the composition mentioned below has been developed.

Mo content as a β stabilizer element is limited within the range of from 2 to 12 at %. This is because the super elastic performance is deteriorated when Mo content is below 2 at % or over 12 at %. In other words, there occurs plastic deformation within a deformed alloy, which makes it difficult for the alloy to recover its original shape. As described above, preferable Mo content is within the range of from 4 to 7 at %. More preferably, Mo content is within the range of from 5 to 6 at %.

Al content as an α stabilizer element is limited within the range of from 3 to 14 at %. This is because the super elastic performance is deteriorated when Al content is below 3 at % or over 14 at %. In other words, there occurs plastic deformation within a deformed alloy, which makes it difficult for the alloy to recover its original shape. Preferable Al content is within the range of from 3 to 9 at %. More preferably, Al content is within the range of from 7 to 9 at %.

Accordingly, a Ti alloy containing Mo from 2 to 12 at % and Al from 3 to 14 at % becomes a super-elastic β solid solution titanium alloy. Therefore, a crystalline structure of the rapidly cooled titanium alloy becomes orthorhombic with excellent transformation behavior, which facilitates hot working and cold working, thereby reducing working cost as compared with Ni—Ti alloys.

Such a Ti—Mo—Al alloy can be manufactured in the same method as that for the aforementioned Ti—Mo—Ga alloy, though the present invention is not limited to this method. In the other words, metals as given alloying components are melted in a consumable electrode arc melting furnace, and cast into required shapes to prepare ingots. Then, in order to remove segregation, thus prepared ingots are subjected to homogenized heat treatment under the conditions that heat treatment environments are preferably vacuum or inert gas environments, heat treatment temperatures preferably range from 1,000 degree to 1,200 degree and the retention time was set within the range of from 10 to 48 hours. After being homogenized heat treated, the ingots are rapidly cooled down to a room temperature with the use of oil or water.

The ingots are cold worked to prepare thin sheets. For the purpose of solution heat treatment of alloying elements, the thin sheets are subjected to solution heat treatment under the following conditions that heat treatment environments are preferably vacuum or inert gas environments, heat treatment temperatures preferably ranges from 600 degree to 1,100 degree and retention time is set within the range of from 1 minute to 10 hours to obtain a super-elastic titanium alloy with α phase finely precipitated.

As yet another embodiment of the present invention a Ti—Mo—Ge alloy is now described. Effects of Mo added to Ti are the same as described in the above embodiments.

When Ge is added to Ti, Al functions as an α stabilizer element, extending α phase region so as to improve the strength at room temperature. Then, development work has been advanced on super-elastic β solid solution titanium alloys having the composition of Ti to which Mo as a β stabilizer element for lowering martensite transformation temperature and Ge as an α stabilizer element are added, which undergoes thermo-elastic martensite transformation upon rapid cooling. As a result, the super-elastic β solid solution titanium alloys with the composition mentioned below has been developed.

Mo content as a β stabilizer element is limited within the range of from 2 to 12 at %. This is because the super elastic performance is deteriorated when Mo content is below 2 at % or over 12 at %. In other words, there occurs plastic deformation within a deformed alloy, which makes it difficult for the alloy to recover its original shape. As described above, preferable Mo content is within the range of from 4 to 7 at %. More preferably, Mo content is within the range of from 5 to 6 at %.

Ge content as an α stabilizer element is limited within the range of from 0.1 to 8 at %. This is because the super elastic performance is deteriorated when Ge content is below 0.1 at % or over 8 at %. In other words, there occurs plastic deformation within a deformed alloy, which makes it difficult for the alloy to recover its original shape. Preferable Ge content is within the range of from 1 to 4 at %. More preferably, Ge content is within the range of from 2 to 4 at %.

Accordingly, a Ti alloy containing Mo from 2 to 12 at % and Ge from 1 to 8 at % becomes a super-elastic β solid solution titanium alloy. Therefore, a crystalline structure of the rapidly cooled titanium alloy becomes orthorhombic with excellent transformation behavior, which facilitates hot working and cold working, thereby reducing working cost as compared with Ni—Ti alloys.

Such a Ti—Mo—Ge alloy can be manufactured in the same method as that for the aforementioned Ti—Mo—Al alloy, though the present invention is not limited to this method. In the other words, metals as given allowing components are melted in a consumable electrode arc melting furnace, and cast into required shapes to prepare ingots. Then, in order to remove segregation, thus prepared ingots are subjected to homogenized heat treatment under the conditions that heat treatment environments are preferably vacuum or inert gas environments, heat treatment temperatures preferably range from 1,000 degree to 1,200 degree and the retention time is set within the range of from 10 to 48 hours. After being homogenized heat treated, the ingots are rapidly cooled down to room temperature with the use of oil or water.

The ingots are cold worked to prepare thin sheets. For the purpose of solution heat treatment of alloying elements, the thin sheets are subjected to solution heat treatment under the following conditions that heat treatment environments are preferably vacuum or inert gas environments, heat treatment temperatures preferably range from 600 degree to 1,100 degree and retention time is set within the range of from 1 minute to 10 hours to obtain a super-elastic titanium alloy with α phase finely precipitated.

EXAMPLES

Example 1

Ti—Mo—Ga alloy ingots with the compositions shown in Table 1 of FIG. 2 were prepared by being melted in a consumable electrode arc melting furnace and cast into required shapes. The ingots were subjected to homogenized heat treatment at a temperature of 1,100 degree for 24 hours of retention time before the ingots were rapidly cooled down with the use of water. Then, the ingots were cold rolled to thickness with 95% reduction and prepared to be sheet materials of 0.4 mm in thickness. Test sample of 1 mm in width and 20 mm in length were cut from the sheet materials. The test samples were held at 1000 degree for one hour and then quenched into a water bath, which results in obtaining super-elastic titanium alloys.

In order to evaluate shape memory effects of the test samples of the super-elastic titanium alloys, the test samples were held at 37 degree, for example by a method of holding them in a constant temperature chamber. The test samples were bent once to have a single turn around a stainless round bar of 10 mm in diameter, and held for 30 seconds while they were bent at 180-degree angle. Then, the test samples were taken off the stainless round bar. After that, bend angles of the resultant test samples which did not recover their original shapes due to plastic deformation were measured thereby to evaluate the shape memory effects.

The procedure of measuring a bend angle is described with reference to FIG. 1. When a test sample of a super-elastic titanium alloy 1 which was wound around a stainless round bar is plastically deformed without recovering its original shape, its deformation is expressed by an angle (θ) 2 relative to the horizontal plane.

Evaluation results of the shape memory effects are also shown in Table 1. When the angle (θ) is below 5-degree angle, the alloy is thought to recover its original shape and exhibits the shape memory effects, which is denoted by a round mark "○" in the table. For the numbers a-7~a-12 in Table 1, since the compositions are outside of the scope of the present invention, super elastic performance is unfavorable and the original shapes are not recovered. On the other hand, for the numbers a-1~a-6 of the present invention, the original shapes are recovered.

Example 2

Ti—Mo—Al alloy ingots with the compositions shown in Table 2 of FIG. 3 were formed into sheet materials of 0.4 mm in thickness in the same method as that in Example 1. Test samples of the super-elastic titanium alloys thus were prepared. Then, shape memory effects of the test samples of the super-elastic titanium alloys were evaluated in the same way as in Example 1. Evaluation results of the shape memory effects are also shown in Table 2. For the numbers b-7~b-12 in Table 2, since the compositions are outside of the scope of the present invention, super elastic performance is unfavorable and the original shapes are not recovered. On the other hand, for the numbers b-1~b-6 of the present invention, the shapes are recovered.

Example 3

Ti—Mo—Ge alloy ingots with the compositions shown in Table 3 of FIG. 4 were formed into sheet materials of 0.4 mm in thickness in the same method as that in Example 1. The test samples of the super-elastic titanium alloys were thus prepared. Then, shape memory effects of the test samples of the super-elastic titanium alloys were evaluated in the same way as in Example 1. Evaluation results of the shape memory effects are also shown in Table 3. For the numbers c-5~c-10 in Table 3, since the compositions are outside of the scope of the present invention, super elastic performance is unfavorable and the original shapes are not recovered. On the other hand, for the numbers c-1~c-4 of the present invention, the shapes are recovered.

As mentioned above, the inventors of the present invention has achieved the super-elastic performance expressed within an alloy of the present invention which is a titanium-based alloy with Mo and further Ga, Al or Ge added thereto. In addition, since an alloy of the present invention is a nickel-free alloy, the alloy is usable in medical applications without causing allergic problems. In other words, a nickel-free alloy of the present invention having super-elastic performance is also suitable for use as materials of medical appliances.

What is claimed is:

1. A method for making a super-elastic titanium alloy for medical use comprising the steps of:

preparing a titanium alloy ingot which consists essentially of:
  molybdenum (Mo) as a β stabilizer element of titanium (Ti)
    :from 2 to 12 at %;
  gallium (Ga) as an α stabilizer element of the titanium (Ti)
    :from 0.1 to 14 at %; and
  the balance being titanium (Ti) and inevitable impurities,
subjecting the ingot to a homogenized heat treatment in a vacuum environment or an inert gas environment at a temperature ranging from 1,000 degree C. to 1,200 degree C., and cooling the ingot quickly to a room temperature;
after cooling the ingot to the room temperature, cold working the ingot to prepare a sheet; and
subjecting the sheet to a solution heat treatment in the vacuum environment or the inert gas environment at a temperature ranging from 600 degree C. to 1,100 degree C.

2. The method as claimed in claim 1, wherein a content of the molybdenum (Mo) is from 4 to 7 at % and a content of the gallium (Ga) is from 1 to 4 at %.

3. The method as claimed in claim 1, wherein a time of the homogenized heat treatment ranges from 10 to 48 hours.

4. The method as claimed in claim 1, wherein a time of the solution heat treatment ranges from 1 minute to 10 hours.

5. A method for making a super-elastic titanium alloy for medical use comprising the steps of:

preparing a titanium alloy ingot which consists essentially of:
  molybdenum (Mo) as a β stabilizer element of titanium (Ti)
    :from 2 to 12 at %;
  germanium (Ge) as an α stabilizer element of the titanium (Ti)
    :from 0.1 to 8 at %; and
  the balance being titanium (Ti) and inevitable impurities,
subjecting the ingot to a homogenized heat treatment in a vacuum environment or an inert gas environment at a temperature ranging from 1,000 degree C. to 1,200 degree C., and cooling the ingot quickly to a room temperature;
after cooling the ingot to the room temperature, cold working the ingot to prepare a sheet; and
subjecting the sheet to a solution heat treatment in the vacuum environment or the inert gas environment at a temperature ranging from 600 degree C. to 1,100 degree C.

6. The method as claimed in claim 5, wherein a content of the molybdenum (Mo) is from 4 to 7 at % and a content of the germanium (Ge) is from 1 to 4 at %.

7. The method as claimed in claim 5, wherein a time of the homogenized heat treatment ranges from 10 to 48 hours.

8. The method as claimed in claim 5, wherein a time of the solution heat treatment ranges from 1 minute to 10 hours.

* * * * *